United States Patent [19]

Panster et al.

[11] Patent Number: 4,645,848

[45] Date of Patent: Feb. 24, 1987

[54] PHENYLENE GROUP-CONTAINING ORGANOPOLYSILOXANES AND METHOD FOR THEIR PREPARATION

[75] Inventors: Peter Panster, Rodenbach; Peter Kleinschmit, Hanau, both of Fed. Rep. of Germany

[73] Assignee: Degussa Aktiengesellschaft, Frankfurt, Fed. Rep. of Germany

[21] Appl. No.: 865,489

[22] Filed: May 21, 1986

[30] Foreign Application Priority Data

May 25, 1985 [DE] Fed. Rep. of Germany ....... 3518879

[51] Int. Cl.$^4$ ............................ C07F 7/08; C07F 5/06; C07F 7/00; C07F 7/28
[52] U.S. Cl. ......................................... 556/9; 556/10; 556/434; 528/9; 528/16; 528/17; 528/33; 528/34; 528/30
[58] Field of Search ................ 556/434, 9, 10; 528/9, 528/16, 17, 33, 34, 30

[56] References Cited

U.S. PATENT DOCUMENTS 3,209,018 9/1965 Merker ............................ 556/434 X
3,304,320 2/1967 Spencer ........................... 556/434 X
4,442,040 4/1984 Panster et al. .................... 556/10 X

*Primary Examiner*—Paul F. Shaver
*Attorney, Agent, or Firm*—Beveridge, DeGrandi & Weilacher

[57] ABSTRACT

Phenylene group-containing organopolysiloxanes formed of a plurality of identical or different units represented by the structural formula:

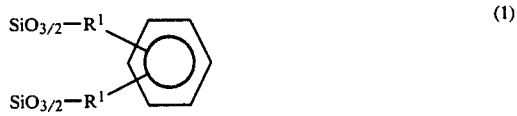

(1)

where in each case all three possible isomers in relation to the position of the $SiO_{3/2}$—$R^1$ substituents on the phenylene group can be present concurrently, in which $R^1$ stands for —$CH_2$—$CH_2$— or $CH_3$—$CH<$ and the free valences of the oxygen atoms are saturated by silicon atoms of other groups of formula (1) and/or by cross-linking bridge groups. A process for the preparation of these polysiloxanes and the use thereof for the synthesis of carriers of active substances is also disclosed.

10 Claims, No Drawings

PHENYLENE GROUP-CONTAINING ORGANOPOLYSILOXANES AND METHOD FOR THEIR PREPARATION

The present invention relates to new phenylene group-containing organopolysiloxanes, which can be modified by introduction of functional groups and thereby converted into carriers of active substances, and a process for the preparation of said organopolysiloxanes.

Active substances or functional groups, which are bound to an insoluble carrier by chemical bonds, possess the likely advantages of easier separability, ability for recycle, and recoverability of the active components in industrial applications in comparison with active substances or functional groups employed in homogeneous phase. In addition, the stability and residence time of an agent modified according to this principle can often be markedly increased and its selectivity desirably influenced. Whereas ion exchangers, for instance, are known classic examples of this concept, enzymes or complex metal catalysts fixed on a carrier, for example, are the subject of more recent investigations and synthesis attempts.

Heretofor, organic polymers, especially polystyrene, have mainly been used as carriers for this purpose. Examples thereof are described, for instance, in British Pat. No. 1,277,736 or in U.S. Pat. No. 3,708,462. Although inorganic polymeric systems such as silicic acid or silica gel have a variety of advantages, they are generally less suitable for this application, since they can be modified by introduction of functional groups only to a limited extent and the functional group can be cleaved rather easily by hydrolytic means.

In the absence of truly suitable carrier systems, attempts have previously been made to anchor phenylsiloxanes on silica gel (cf. J. Conan, M.. Batholin, and A. Guyet, J. Mol, Catal. 1, 375, 1975/76). In principle, however, such systems possess the same disadvantages as pure inorganic carriers themselves.

Therefore, the present invention has as its object the provision of carrier systems that combine both the advantages of the organic as well as of the inorganic carrier materials; i.e., they possess a fixed, rigid structure and high resistance to temperature and aging, so they swell only to a limited extent or not at all, are insoluble in organic solvents, and can be transformed into carriers for active substances by introduction of functional groups.

This object is achieved by the development of new phenylene group-containing organopolysiloxanes, which can be readily modified by introduction of functional groups at the phenylene groups according to known concepts in organic synthesis and can be modified in the manner and to the extent desired into a carrier for active substances or active groups. The new phenylene group-containing organopolysiloxanes are characterized by the fact that they comprise a plurality of identical or different units represented by the structural formula:

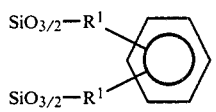  (1)

in which all three possible isomers in relation to the position of the $SiO_{3/2}$—$R^1$ substituents on the phenylene group can be present concurrently, the bridge groups $R^1$ represent the groups —$CH_2$—$CH_2$— or $CH_3$—$CH<$ and can be identical or different, and the free valences of the oxygen atoms are saturated by silicon atoms of other groups of formula (1) and/or by cross-linking bridge groups:

$SiO_{4/2}$ or $R'SiO_{3/2}$ or $R_2'SiO_{2/2}$ or
$TiO_{4/2}$ or $R'TiO_{3/2}$ or $R_2'TiO_{2/2}$ or
$ZrO_{4/2}$ or $R'ZrO_{3/2}$ or $R_2'ZrO_{2/2}$ or
$AlO_{3/2}$ or $R'AlO_{2/2}$ in which $R'$ is a methyl or ethyl group, and the ratio of the sum of Si atoms in formula (1) to the bridge atoms silicon, titanium, zirconium, and aluminum can be 1:0 to 1:15.

The position of the two $SiO_{3/2}$—$R^1$ substituents relative to each other on the phenylene group is generally of secondary importance; an ortho, a meta and a para position can be present. In general, with the object of achieving as high a capacity as possible in relation to the functional groups or active substance groups to be fixed later on the phenylene groups, it is desirable that no cross-linking bridge groups of the indicated type mentioned above be present in the polymeric structure, since they do not contribute to the functionality.

However, in various cases, e.g., when using the polysiloxanes according to the invention as carriers of heterogeneous complex catalysts, it can be advantageous, for example for the purpose of controlling the density of the active substance groups or for influencing and setting certain specific surfaces or porosities, or also certain steric relationships or surface properties to incorporate cross-linking bridge groups of the above type into the skeleton. Also, the presence of the cross-linking agents may be of interest, for example, because of certain catalytic properties thereof.

Another object of the invention is a process for the preparation of new phenylene group-containing organopolysiloxanes. It is characterized in that a silane of the general formula:

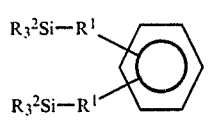  (2)

in which the bridge groups $R^1$ represent the groups —$CH_2$—$CH_2$— or $CH_3$—$CH<$ and can be identical or different, and the substituents $R_2$ represent a linear or branched alkoxy group having 1 to 3 carbon atoms or chloride, and can be identical or different, if necessary after the addition of a solvent and/or cross-linking agent precursor of the general formula:

in which
Me=Si, Ti, Zr, or Al,
$R^3$ represents a linear or branched alkoxy residue having 1 to 5 carbon atoms or chloride and
$R'$ is a methyl or ethyl group,
is hydrolyzed and polycondensed with stoichiometric or excess amounts of water, the product is separated from the liquid phase optionally after addition of another solvent, is then washed, optionally, under a protective gas atmosphere or in vacuum up to a temperature of 200° C., then optionally tempered for 1 hour to 5 days at temperature of 100°–400° C., in air or under a protective gas, at standard pressure in vacuum or at gage pressure, then optionally ground and classified.

With respect to the stability of the new phenylene group-containing organopolysiloxanes vis-a-vis partial or total solution at elevated temperature in water or aggressive polar organic solvents, it is of advantage to expose the product to said tempering after its preparation, optionally coupled with drying or just before use of the product. The process of tempering is known from the synthesis of inorganic polymers such as, for example, silicic acids or silica gels. It causes further dehydration upon reaction of neighboring silanol groups or cleavage of alkoxy groups still present in the polymeric substance or Si-bound chlorine atoms in the form of the corresponding alcohol or hydrogen chloride with concurrent formation of siloxane bonds.

In principle, $R_2$ represents other substituents such as, for example, Br, I, $OC_6H_5$ or $OC_2H_4OCH_3$, yet the use thereof offers no advantages, but rather disadvantages, for example, with respect to the accessibility of the corresponding silanes or in regard to the hydrolysis of the corresponding silanes or in regard to the hydrolysis rate and the by-products formed during hydrolysis. Occassionally, partly as a function of the type of solubilizer employed and when $R^2$ represents a linear or branched alkoxy residue, it is advantageous to add a small amount of a typical polycondensation catalyst, in the simplest case aqueous HCl solution, to the silane to be polycondensed. From this point of view, the hydrolysis rate is understandably highest when $R^2$ represents chloride.

Although the hydrolysis and polycondensation can be carried out without the use of a solubilizer, the employment thereof is generally preferable for practical reasons.

The alcohols corresponding to the alkoxy residues are suitable as solvents especially if $R^2$ represents a linear or branched alkoxy group with 1 to 3 carbon atoms. Admittedly, other solvents that do not react with the silane can also be used such as, for instance, toluene, xylene, chlorinated hydrocarbons, nitromethane, nitrobenzene, acetone, methyl ethyl ketone, diethyl ketone, higher alcohols, diethyl ether, di-n-propyl ether, diisopropyl ether, di-n-butyl ether, methyl-tert-butyl ether, aliphatic, linear, branched, or cyclic hydrocarbons, dimethyl sulfoxide, and dimethylformamide. Any suitable solvent that are inert under the conditions of the reaction may be used.

If a cross-linking agent precursor is added, the minimum amount of water to be used, i.e., the stoichiometric amount, is adjusted accordingly. Needless to say that the hydrolysis and polycondensation can be carried out not only at standard pressure, but also at subatmospheric or gauge pressure.

The product can be separated from the liquid phase by any suitable technique, either by distilling the liquid off or filtering or centrifuging the solid.

The novel organopolysiloxanes have specific surfaces of less than 1 m²/g to 1000 m²/g depending on the starting material, polycondensation medium employed, and polycondensation conditions. The particle size of the solid product can be adjusted within certain ranges; typically they range from about 0.1 micron to 1 cm.

Another object of the invention is the use of the novel phenylene group-containing organopolysiloxanes for the synthesis of carriers of active substances by substitution of at least one of the hydrogen atoms on the ring by substituents that modify the functionality of the carrier, in accordance with conventional methods employed in organic chemistry.

The invention will now be described in further detail with reference to the following illustrative examples.

EXAMPLE 1

100 g of an isomeric compound comprising up to about 90% by weight of the ortho-, meta-, para-isomer mixture (12% by weight/65% by weight/23% by weight) of the chlorosilane:

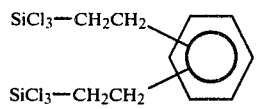

and up to about 10% of the chlorosilanes

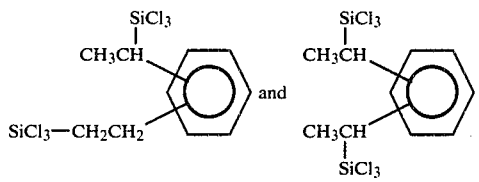

(2:1 distribution of amounts by weight)

with the same isomer distribution was dissolved in about 100 ml of toluene. The solution was combined with 100 g of desalinated water over a 30 minute period in a 1 liter three-neck flask with a KPG stirrer and a reflux condenser with vigorous stirring and initially with ice cooling. Spontaneous thickening occurred with considerable foaming immediately after addition of 30 ml of H₂O, so that the flask content could no longer be stirred within a short time. After addition of another 50 ml of toluene and 50 ml of water, the mixture was heated to reflux temperature and stirred for 2 hours. The mixture was then cooled and the resulting white solid was filtered through a suction filter, and washed initially with 100 ml of ethanol, then with 3 liters of water until it was almost free of HCl. After 12 hours of drying at 150° C./100 mbar and 30 hours of tempering at 250° C. under an N₂ atmosphere, there was obtained 58.8 g (99.8% of the theoretical) of the desired phenylene group-containing organopolysiloxane, comprising up to about 90% of units of the formula:

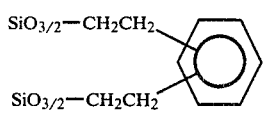

and up to about 10% of units of the formula:

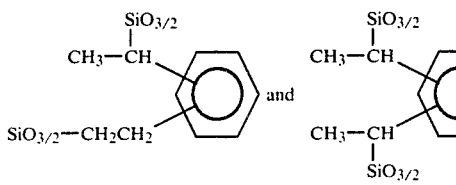

(corresponding to the distribution of amounts by weight determined for the starting material)

in the form of a white powder.

| Elemental analyses: | % C | % H | % Si | % Cl |
|---|---|---|---|---|
| Theoretical: | 50.81 | 5.12 | 23.76 | 0 |
| Found: | 48.95 | 5.33 | 22.47 | 0.02 |

After drying and tempering, the product was ground and classified. The 0.3–1.2 mm particle size fraction was used in the determination of the specific surface area by an area meter, which gave a value of 338 m²/g. A DSC analysis of the product under an $N_2$ atmosphere yielded an incipient endothermic decomposition of the polymer at a temperature in excess of 280° C.

EXAMPLE 2

100 g of an isomer compound comprising up to about 90% by weight of the ortho-, meta-, para-isomer mixture (12% by weight/65% by weight/23% by weight) of the ethoxysilane:

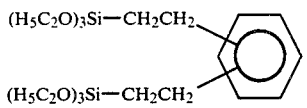

and up to about 10% of the ethoxysilanes

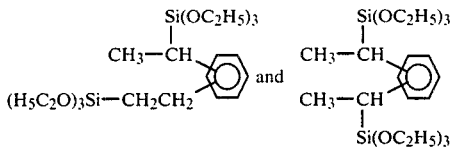

(2:1 distribution of amounts by weight)

with the same isomeric distribution was mixed with 120 ml of ethanol. The mixture was heated in a 1 liter three-neck flask with a KPG stirrer, a reflux condenser, and dropping funnel to reflux temperature, and combined with 50 ml of $H_2O$ all at once with vigorous stirring. Just a few minutes after the addition of water, the batch thickened and a voluminous solid appeared. This was stirred for another 2 hours at reflux, then filtered through a suction filter, and washed first with 100 ml of ethanol, then with 2 liters of $H_2O$. After 24 hours of drying at 150° C./100 mbar, 52.7 g (102.3% of the theoretical) of the desired product was obtained in the form of a white solid. The composition of this organopolysiloxane corresponded to that of the product obtained in Example 1, both in regard to structure and in relation to the isomer distribution.

| Elemental analyses: | % C | % H | % Si |
|---|---|---|---|
| Theoretical: | 50.81 | 5.12 | 23.76 |
| Found: | 49.03 | 6.01 | 22.34 |

The 0.3–1.2 mm fraction of the classified product had a specific surface area of 89 m²/g (area meter).

EXAMPLE 3

75 g of the starting material used in Example 2 and 68.12 g of $Si(OC_2H_5)_4$ were combined in 100 ml of ethanol. The mixture was heated in a 1 liter three-neck flask with a KPG stirrer, a reflux condenser, and dropping funnel to reflux temperature. 50 g of water was added all at once with vigorous stirring. The flask content gelled immediately after the water was added. The flask content was stirred for another hour at reflux, then cooled, filtered off, and washed with 300 ml of ethanol. After 10 hours of drying at 150° C. and 2 hours of tempering at 300° C. under an $N_2$ atmosphere, there was obtained 58.9 g (101.0% of the theoretical) of a polymer product, comprising up to about 90% of units of the formula:

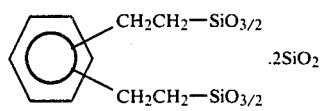

and up to about 10% of units of the formula:

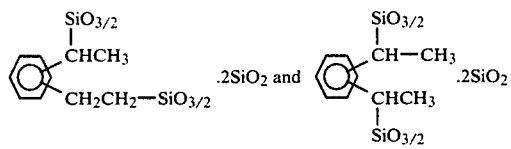

(corresponding to the distribution of amounts by weight determined for the starting material)

with an ortho-/meta-/para-isomer ratio of 12% by weight/65% by weight/23% by weight.

| Elemental analyses: | % C | % H | % Si |
|---|---|---|---|
| Theoretical: | 33.69 | 3.39 | 31.51 |
| Found: | 32.21 | 3.56 | 30.87 |

EXAMPLE 4

75 g of an isomer compound, comprising up to about 100% of the meta- and para-isomer mixture (60% by weight/40% by weight) of the methoxysilane:

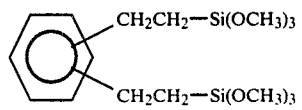

and 29.7 g of $(H_3C)_2Si(OC_2H_5)_2$ were combined in 100 ml of acetone. The mixture was heated in a 1 liter three-neck flask with a KPG stirrer, a reflux condenser, and dropping funnel to reflux temperature. Then 40 g of water was added all at once. After a short time, a voluminous solid formed in the flask, which was stirred for another hour at reflux, then centrifuged, washed with 250 ml of aceotne, and dried for 15 hours at 150° C. After 24 hours of tempering at 250° C. under an N₂ atmosphere, there was obtained 61.9 g (99.6% of the theoretical) of the desired polymer product, consisting of units of the formula:

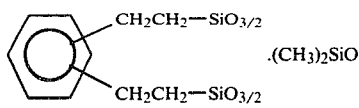

in the form of a white, partially lumpy solid.

| Elemental analyses: | % C | % H | % Si |
|---|---|---|---|
| Theoretical: | 46.41 | 5.84 | 27.13 |
| Found: | 45.22 | 5.82 | 26.71 |

EXAMPLE 5

Starting with 50 g of the phenylene group-containing organosilanes used in Example 4, 113.8 g of Ti(O-iso-C₃H₇)₄, 100 ml of isopropanol, and 50 ml of water, as in Example 4, there was obtained 63.3 g (99.6% of the theoretical) of a polymeric product, consisting of units of the formula:

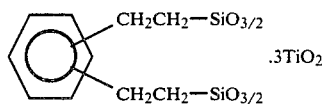

in the form of a white solid.

| Elemental analyses: | % C | % H | % Si | % Ti |
|---|---|---|---|---|
| Theoretical: | 25.23 | 2.54 | 11.80 | 30.18 |
| Found: | 24.60 | 2.67 | 10.95 | 29.49 |

EXAMPLE 6

Starting with 60 g of a phenylene group-containing organosilane, comprising up to about 100% of the ortho- and meta-isomer mixture (60% by weight/40% by weight) of the ethoxysilane:

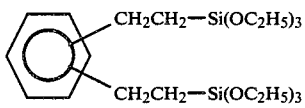

42.8 g of Zr(O—nC₃H₇)₄, 100 ml of ethanol, and 40 ml of water, as in Example 4, there was obtained 46.3 g (98.4% of the theoretical) of a polymeric product, consisting of units of the formula:

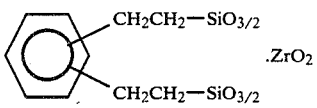

in the form of a white solid.

| Elemental analyses: | % C | % H | % Si | % Zr |
|---|---|---|---|---|
| Theoretical: | 33.40 | 3.36 | 15.62 | 25.37 |
| Found: | 32.95 | 3.87 | 15.20 | 24.29 |

EXAMPLE 7

Starting with 100 g of the organosilane used in Example 6, 44.1 g of (H₅C₂)Al(O—C₄H₉)₂, 100 ml of ethanol, and 40 ml of H₂O, as in Example 4, there was obtained 67.0 g (99.7% of the theoretical) of a polymer product, consisting of units of the formula:

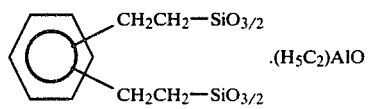

| Elemental analyses: | % C | % H | % Si | % Al |
|---|---|---|---|---|
| Theoretical: | 46.73 | 5.56 | 18.21 | 8.75 |
| Found: | 45.68 | 5.50 | 17.36 | 8.44 |

Further variations and modifications of the invention will be apparent to those skilled in the art from the foregoing description and are intended to be encompassed by the appended claims.

The German priority application P 35 18 879.0 is relied on and incorporated herein by reference.

We claim:

1. A phenylene group-containing organopolysiloxane comprising a plurality of identical or different units represented by the structural formula:

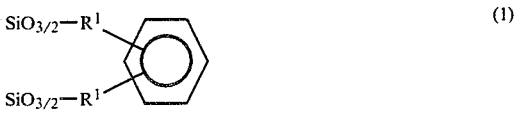

(1)

where in each case all three possible isomers in relation to the position of the SiO₃/₂—R¹ substituents on the phenylene group can be present concurrently, in which the bridge groups R¹ represent —CH₂—CH₂— or CH₃—CH< and can be identical or different, and the free valences of the oxygen atoms are saturated by silicon atoms of other groups of formula (1) and/or by cross-linking bridge groups:

SiO₄/₂ or R'SiO₃/₂ or R₂'SiO₂/₂ or
TiO₄/₂ or R'TiO₃/₂ or R₂'TiO₂/₂ or
ZrO₄/₂ or R'ZrO₃/₂ or R₂'ZrO₂/₂ or
AlO₃/₂ or R'AlO₂/₂ in which R' is a methyl or ethyl group, and the ratio of the sum of the Si atoms in formula (1) to the bridge atoms silicon, titanium, zirconium, and aluminum can be 1:0 to 1:15.

2. A process for the preparation of compounds according to claim 1, comprising hydrolyzing and polycondensing a silane represented by the structural formula:

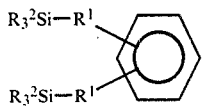 (2)

in which the bridge groups $R^1$ represent the groups —$CH_2$—$CH_2$— or $CH_3$—$CH<$ and can be identical or different, and the substituents $R_2$ represent a linear or branched alkoxy group having 1 to 3 carbon atoms, or chloride, and can be identical or different, with stoichiometric or excess amounts of water.

3. The process according to claim 2 wherein the reaction is carried out in the presence of a solvent and/or a cross-linking agent precursor of the general formula:

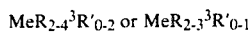

in which
  Me=Si, Ti, Zr or Al,
  $R^3$ represents a linear or branched alkoxy group having 1 to 5 carbon atoms or chloride and
  $R'$ is a methyl or ethyl group.

4. The process according to claim 2 further comprising separating the product from the liquid phase after the addition of another solvent.

5. The process according to claim 2 further comprising washing and drying the product.

6. The process according to claim 5 wherein the drying is carried out under a protective atmosphere or in vacuum at a temperature of up to 200° C.

7. The process according to claim 2 further comprising tempering for 1 hour to 5 days at temperatures of 100°–400° C., in air or under a protective gas, at standard pressure, in vacuum or at gage pressure.

8. The process according to claim 5 further comprising grinding the dried product.

9. The process according to claim 8 further comprising classifying the ground product.

10. The process of claim 3, wherein the solvent is a member selected from the group consisting of methanol, ethanol, n-propanol and isopropanol, n-butanol and isobutanol, n-pentanol, toluene, xylene, chlorinated hydrocarbons, acetone, and dialkyl ether.

* * * * *